United States Patent
Roger et al.

(10) Patent No.: US 8,480,674 B1
(45) Date of Patent: Jul. 9, 2013

(54) ANGLED REAMER SPINDLE FOR MINIMALLY INVASIVE HIP REPLACEMENT SURGERY

(75) Inventors: Douglas J. Roger, Rancho Mirage, CA (US); Philippe Fehlbaum, Lignieres (CH); Yann Rosse, La Neuveville (CH)

(73) Assignee: Greatbatch Medical S.A., Orvin (CH)

(*) Notice: Subject to any disclaimer, the term of this patent is extended or adjusted under 35 U.S.C. 154(b) by 82 days.

(21) Appl. No.: 13/187,924

(22) Filed: Jul. 21, 2011

Related U.S. Application Data

(62) Division of application No. 13/032,764, filed on Feb. 23, 2011.

(60) Provisional application No. 61/307,295, filed on Feb. 23, 2010, provisional application No. 61/348,869, filed on May 27, 2010.

(51) Int. Cl.
*A61F 2/00* (2006.01)

(52) U.S. Cl.
USPC .............................. 606/80; 606/91

(58) Field of Classification Search
USPC ................. 606/79–81, 89, 91, 157–159, 180; 623/22.12; 403/57, 74
See application file for complete search history.

(56) References Cited

U.S. PATENT DOCUMENTS

| | | | |
|---|---|---|---|
| 5,190,422 A | 3/1993 | Lechot | |
| 5,658,290 A | 8/1997 | Lechot | |
| 6,264,647 B1 | 7/2001 | Lechot | |
| 6,506,000 B2 | 1/2003 | Lechot | |
| 6,540,739 B2 | 4/2003 | Lechot | |
| 6,631,653 B2 * | 10/2003 | Brickner et al. | .......... 74/471 XY |
| 6,669,702 B2 | 12/2003 | Lechot | |
| 6,689,138 B2 | 2/2004 | Lechot | |
| 7,056,317 B2 | 6/2006 | Lechot | |
| 7,150,751 B2 | 12/2006 | Lechot | |
| 7,229,078 B2 | 6/2007 | Lechot | |
| 7,326,198 B2 | 2/2008 | Desarzens et al. | |
| 7,572,259 B2 | 8/2009 | Desarzens et al. | |
| 7,637,909 B2 | 12/2009 | Lechot et al. | |
| 7,682,363 B2 | 3/2010 | Burgi et al. | |
| 7,749,227 B2 | 7/2010 | Lechot et al. | |
| 7,780,669 B2 | 8/2010 | Lechot et al. | |
| 7,785,329 B2 | 8/2010 | Lechot et al. | |
| 7,918,856 B2 | 4/2011 | Guelat et al. | |
| 7,955,320 B2 | 6/2011 | Desarzens et al. | |
| 7,955,323 B2 | 6/2011 | Lechot | |
| 2001/0006593 A1 | 7/2001 | Lechot | |
| 2002/0002365 A1 | 1/2002 | Lechot | |
| 2002/0111632 A1 | 8/2002 | Lechot | |
| 2004/0064141 A1 | 4/2004 | Lechot | |
| 2004/0087958 A1 | 5/2004 | Myers et al. | |
| 2004/0102763 A1 | 5/2004 | Lechot | |
| 2005/0124981 A1 | 6/2005 | Desarzens et al. | |
| 2005/0131395 A1 | 6/2005 | Lechot | |
| 2005/0216020 A1 * | 9/2005 | Orton | .............................. 606/80 |
| 2005/0216022 A1 | 9/2005 | Lechot et al. | |

(Continued)

*Primary Examiner* — Matthew Lawson
(74) *Attorney, Agent, or Firm* — Michael F. Scalise

(57) ABSTRACT

A reamer for use in minimally invasive hip replacement surgical approaches is provided. The reamer spindle includes an elongate housing portion that extends along a first axis and a neck or distal portion that extends along a second axis, wherein the second axis extends at an angle of between about 35 degrees and about 65 degrees relative to the first axis. A reamer head is removably connectable to the distal neck portion and has a surface configured to cut bone.

24 Claims, 16 Drawing Sheets

U.S. PATENT DOCUMENTS

| | | |
|---|---|---|
| 2005/0240192 A1 | 10/2005 | Lechot et al. |
| 2005/0251145 A1 | 11/2005 | Desarzens et al. |
| 2006/0149285 A1 | 7/2006 | Burgi et al. |
| 2007/0083208 A1 | 4/2007 | Desarzens et al. |
| 2007/0173847 A1 | 7/2007 | Guelat et al. |
| 2007/0203477 A1 | 8/2007 | Lechot |
| 2008/0058804 A1 * | 3/2008 | Lechot et al. .................. 606/53 |
| 2008/0065081 A1 | 3/2008 | Lechot et al. |
| 2008/0108999 A1 | 5/2008 | Desarzens et al. |
| 2008/0177265 A1 | 7/2008 | Lechot |
| 2008/0195101 A1 | 8/2008 | Lechot et al. |
| 2008/0300600 A1 | 12/2008 | Guelat et al. |
| 2009/0138016 A1 | 5/2009 | Berthusen et al. |
| 2009/0192515 A1 | 7/2009 | Lechot et al. |
| 2009/0318922 A9 | 12/2009 | Lechot et al. |
| 2010/0204702 A1 | 8/2010 | Lechot et al. |

* cited by examiner

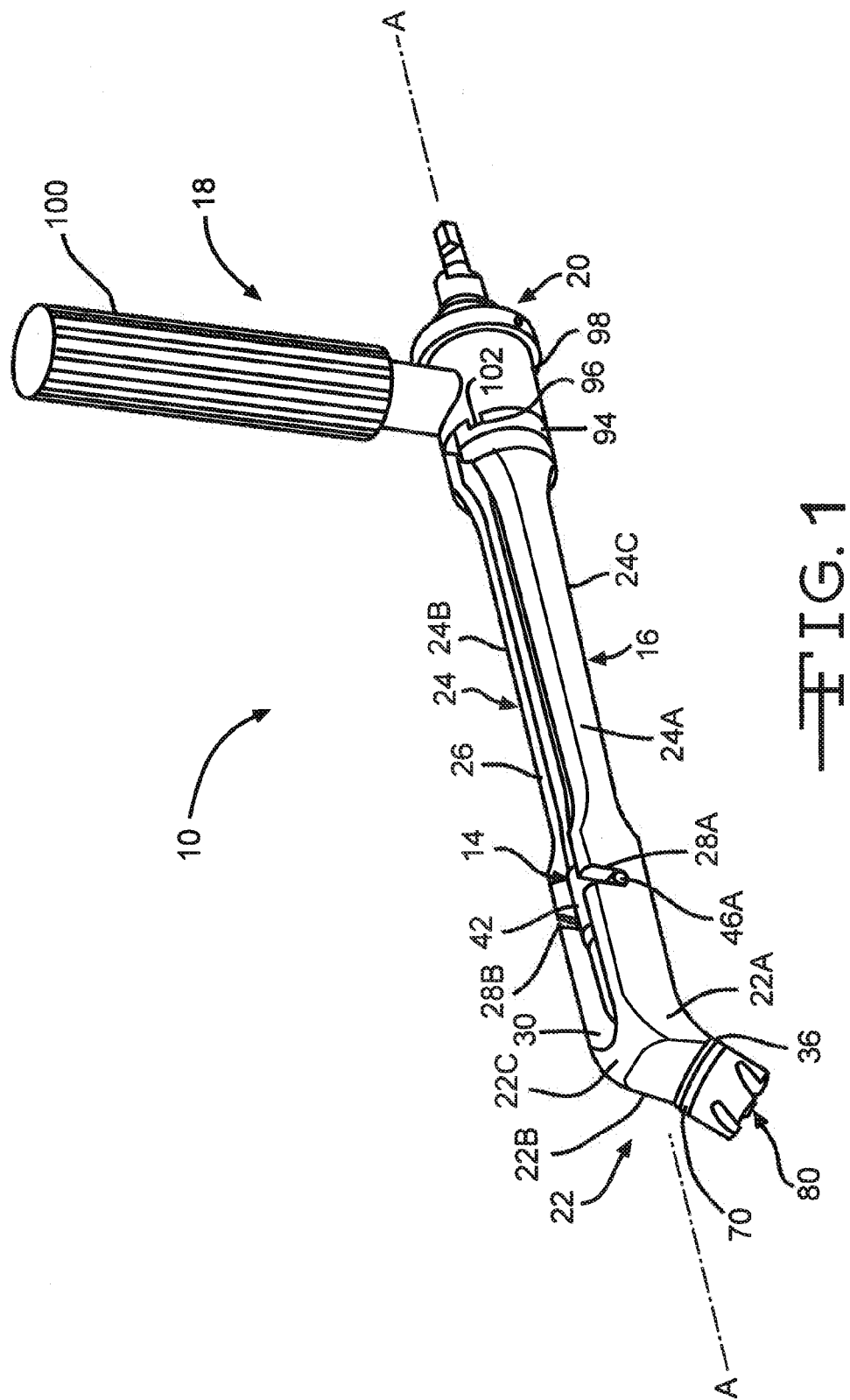

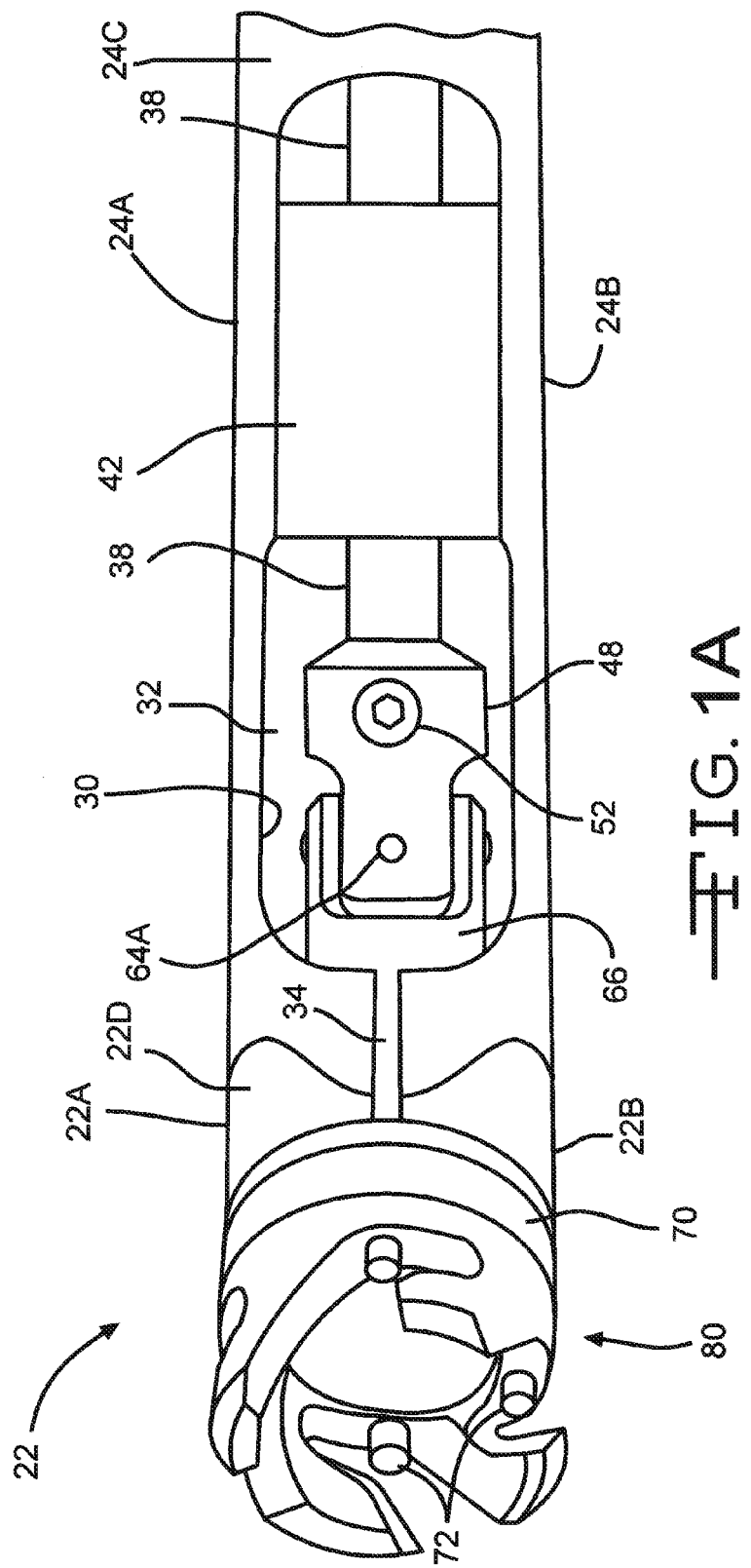

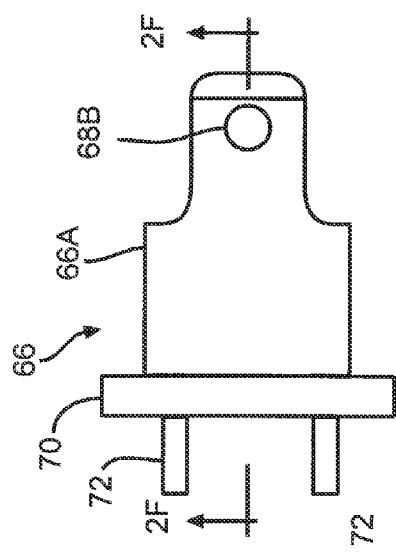
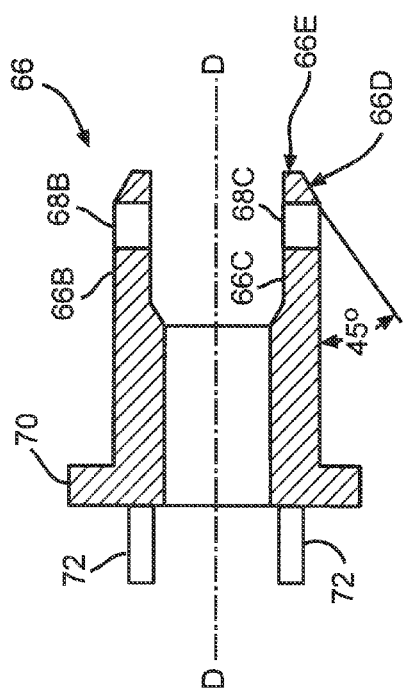

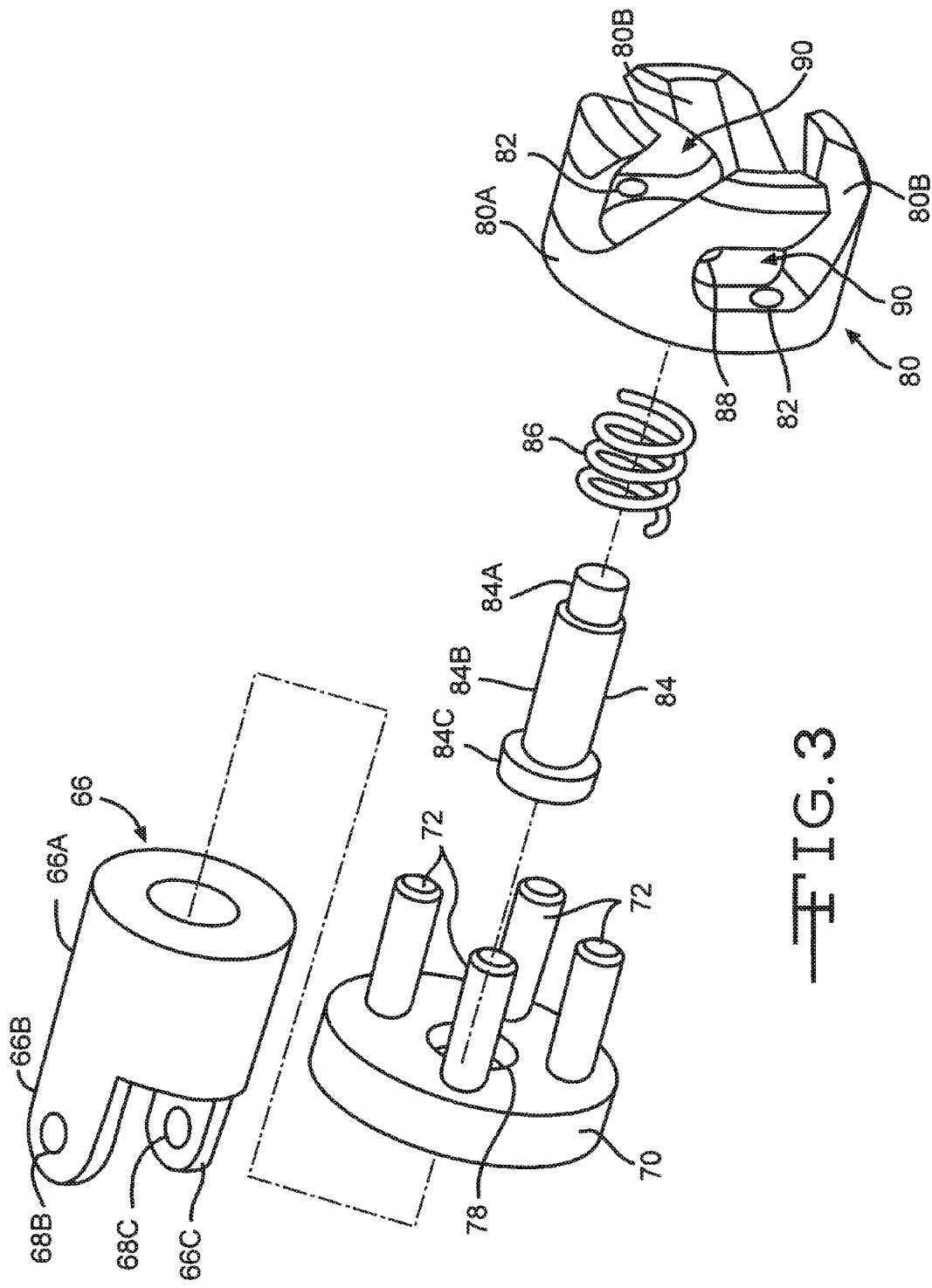

US 8,480,674 B1

ANGLED REAMER SPINDLE FOR MINIMALLY INVASIVE HIP REPLACEMENT SURGERY

CROSS REFERENCE TO RELATED APPLICATIONS

This application is a divisional of U.S. patent application Ser. No. 13/032,764, filed Feb. 23, 2011, which claims priority to U.S. provisional application Ser. Nos. 61/307,295, filed on Feb. 23, 2010 and 61/348,869, filed on May 27, 2010.

BACKGROUND OF THE INVENTION

Nearly 200,000 hip replacements are performed each year in the United States and the number is expected to continue to grow as the population ages. The usual reasons for hip replacement are osteoarthritis, rheumatoid arthritis and traumatic arthritis, all of which can cause pain and stiffness that limit mobility and the ability to perform daily living activities. Hip replacement surgery is usually performed when other measures (e.g., physical therapy, medications, and walking aids) are unable to overcome the chronic pain and disability associated with these conditions.

Various techniques are used by orthopedic surgeons to perform hip replacements. These include the following approaches: anterior, antero-lateral, anterior, posterior, and postero-lateral. The posterior and posteolateral approaches account for approximately 60% to 70% of hip replacement surgeries.

Traditional hip replacement surgery involves an open procedure and extensive surgical dissection. However, such procedures require a longer recovery period and rehabilitation time for the patient. The average hospital stay for open hip replacement procedures is 4-5 days, followed in most cases by extensive rehabilitation.

More recently, there has been considerable interest and research done in Minimally invasive Surgery (MIS), including the use of MIS procedures in connection with hip replacement surgery. In comparison with the traditional open surgical approach, MIS hip replacement surgeries involve fewer traumas to the muscles surrounding the hip joint. Specifically, fewer muscles that help to stabilize the hip joint are cut in MIS hip replacement surgeries, reducing the risk of dislocation of the hip surgery and speeding recovery. Patients spend less time in the hospital and return to normal life activities more quickly.

MIS approaches use smaller surgical fields, which require smaller instruments to perform the hip replacement procedures. One such instrument is a reamer spindle detachably connected to a surgical reamer. The surgical reamer is used to shape the bone of the acetabulum. However, reamer spindles have typically been straight and used in surgical exposures that cut quite a bit of muscle and are, therefore, unsuitable for MIS approaches. Accordingly, there is a need for an improved reamer spindle for use in MIS hip replacement surgical approaches.

SUMMARY OF THE INVENTION

In accordance with one embodiment, a reamer for use in minimally invasive hip replacement surgical approaches is provided. The reamer spindle includes an elongate housing portion that extends along a first axis and a neck or distal portion that extends along a second axis, wherein the second axis extends at an angle of between about 35 degrees and about 65 degrees relative to the first axis. A reamer head is removably connectable to the distal neck portion and has a surface configured to cut bone.

In accordance with another embodiment, the reamer neck can have a length of between about 25 mm and about 35 mm from the intersection of the first and second axes and the distal end of the reamer head.

In accordance with still another embodiment, the elongate housing portion meets the distal neck portion at a rounded low profile surface configured to inhibit trauma to muscle tissue during use of the reamer spindle.

In accordance with yet another embodiment, the reamer can be driven by a source of rotational power, which may be an electric source. A housing is configured to enclose a rotatable shaft connectable to the reamer with the proximal end of the shaft being removably connectable to the source of rotational power. The housing can be a metal (e.g., stainless steel), super alloy or composite casing.

In accordance with another embodiment, the reamer spindle is configured in a way that it can be sterilized between uses.

BRIEF DESCRIPTION OF THE DRAWINGS

FIG. 1 is a perspective view of a reamer spindle 10 according to the present invention.

FIG. 1A is a bottom plan view of the drive train 14 contained in the housing 16 with a reamer connection crown 80 connected to the drive train.

FIG. 2E is an enlarged view of a distal U-joint 66 for the drive train 14.

FIG. 2F is a cross-sectional view taken along line 2F-2F of FIG. 2E.

FIG. 3 is an exploded and enlarged view showing the connection structure of the distal. U-joint 66 to a reamer connection crown 80.

DETAILED DESCRIPTION OF THE PREFERRED EMBODIMENTS

Figure 7:
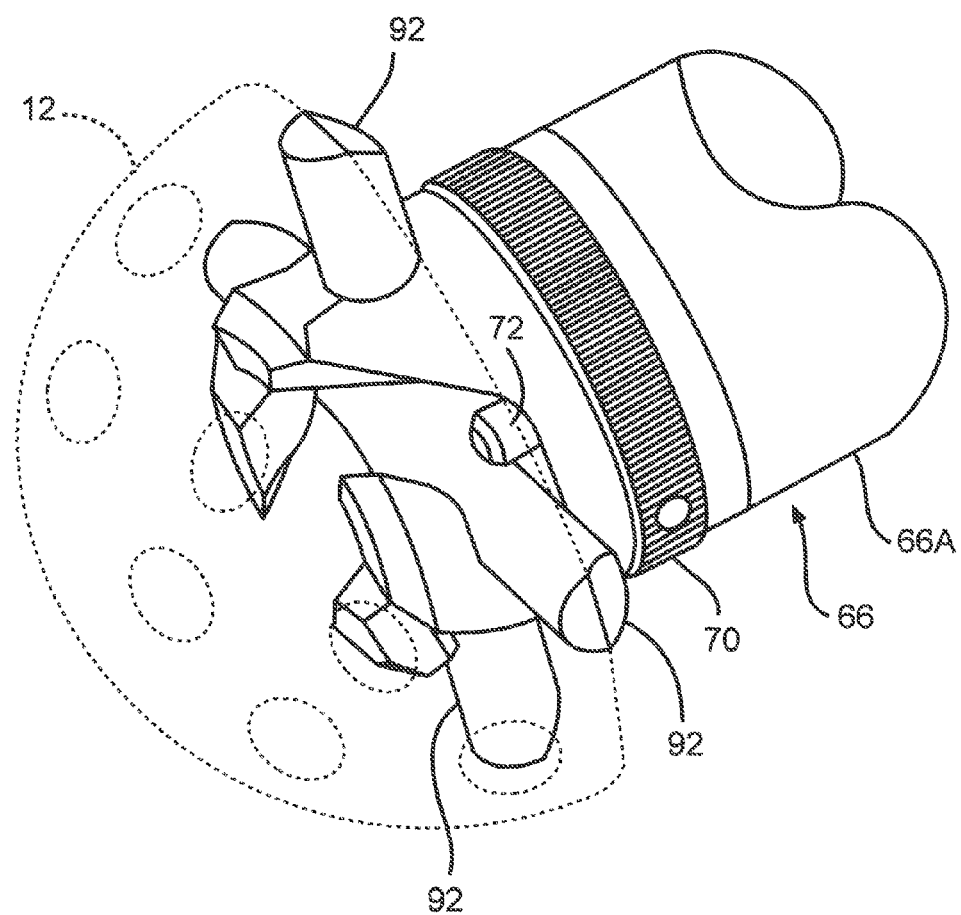
FIG. 7 is an enlarged perspective view of the distal U-joint 66 and connection crown 80 in a closely spaced relationship with a reamer 12 shown in phantom attached thereto.

Turning now to the drawings, FIGS. 1 to 3, 3A to 3F and 4 to 9 illustrate a reamer spindle 10 according to the present invention. The reamer spindle 10 is shown connected to a reamer (FIGS. 4 and 7) for performing a minimally invasive hip replacement surgery. The reamer spindle 10 generally comprises a drive train 14 disposed within a housing 16. A handle assembly 18 is adjustably connected to the housing 16 spaced from the reamer 12.

The housing 16 had a length that extends from a proximal housing section 20 to a distal neck section 22 with an intermediate housing section 24 there between. The intermediate housing section 24 comprises spaced apart right and left side walls 24A and 24B extending upwardly from a bottom wall 24C to an upper opening 26. This construction provides the intermediate section 24 with a generally U-shaped cross-section perpendicular to a longitudinal axis A-A extending along the proximal and intermediate housing sections 20 and 24, but not along the distal section 22. A pair of aligned slots 28A, 28B extends from the upper opening 26 part-way into the height of the respective side walls 24A, 248.

The side walls 24A, 24B and the bottom wall 24C of the intermediate housing section 24 meet the proximal housing section 20 having a partially annularly shaped side wall 20A. The annular side wall 20A has an upper opening 30 aligned with the upper opening 26 of the intermediate handle section 24.

The distal neck section 22 of the housing 16 is angled in a downwardly direction away from the longitudinal axis A-A and the upper opening 26 of the intermediate section 24. In that respect, the right and left side walls 24A, 24B of the intermediate housing section 22 seamlessly form into the right and left side walls 22A and 22B extending distally and downwardly to form the distal neck section 22. However, the bottom wall 24C of the intermediate section 24 ends spaced from the distal neck section 22. This provides an intermediate lower open slot 32 that is vertically below the aligned slots 28A, 28B.

The right and left side walls 22A, 22B meet an upper wall 22C of the distal neck section 22. Potions of a lower distal side wall 22D extend from the right and left walls 22A, 22B. This forms a distal open slot 34 that is not as wide as the intermediate slot 32 in the intermediate section 24 or a forward opening 36 formed by the right and left side walls 22A, 22B, the upper wall 22C and the partial lower wall 22D at the end of the distal neck section 22. The significance of the open slots 32 and 34 will be described hereinafter with respect to partial disassembly of the drive train 14 from the housing 16 for cleaning.

As particularly shown in FIGS. 2 and 2A to 2F, the drive train 14 comprises a major shaft 38 as a cylindrically-shaped member having a proximal portion 40 and a distal end 38A with a length there between. The proximal shaft portion 40 comprises a series of two cylindrical sections 40A, 40B and 40C that step down in diameter as they progress toward the shaft 38 and its proximal end 38B. The proximal shaft end 38A has a hexagonal or similar type structure that provides flats for detachable connection to the chuck of a source of rotary drive power (not shown).

A partially cylindrical sleeve 42 is positioned on the major shaft 38 in an axially slidable relationship therewith. Preferably, a polymeric inner sleeve 44 is disposed between the shaft 38 and an inner surface of the sleeve 42 to facilitate sliding movement of the sleeve 42 along the shaft 38. The outer sidewall of the sleeve 42 is provided with diametrically opposed planar surfaces 42A and 42B that support respective pins 46A, 46B. The pins 46A, 46B extend outwardly from the sleeve 42. They are received in the respective vertically aligned slots 28A, 28B in the side walls 24A, 248 of the intermediate section 24 of the housing 16 with their respective axes aligned with each other and perpendicular to the longitudinal axis A-A of the major shaft 38. The pins 46A, 46B received in the slots 28A, 28B provide stability to the drive train 14 as it rotates during a MIS procedure.

Figure 2:
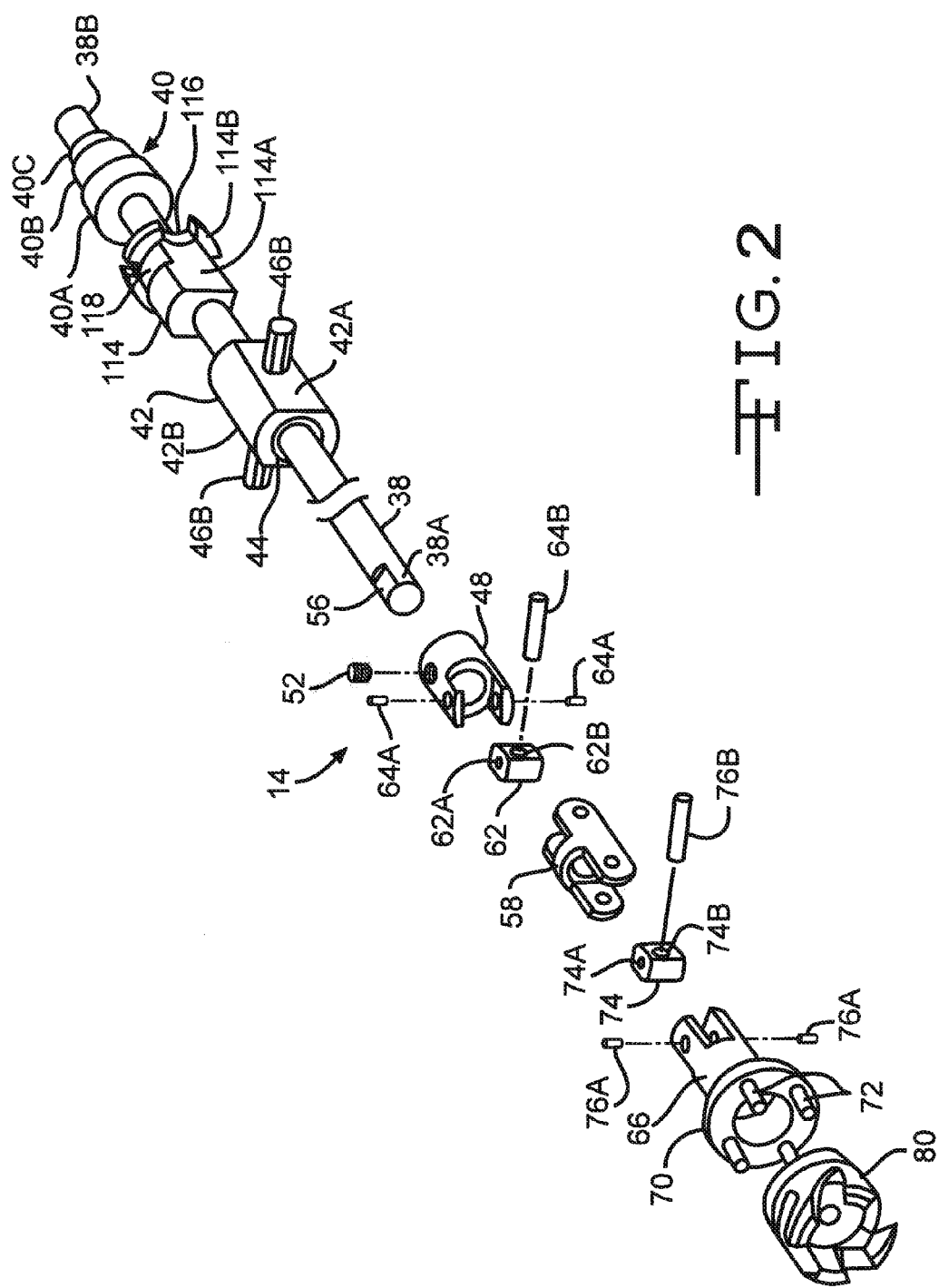
FIG. 2 is an exploded view of a drive shaft 14 for the reamer spindle 10.
Figure 2A:
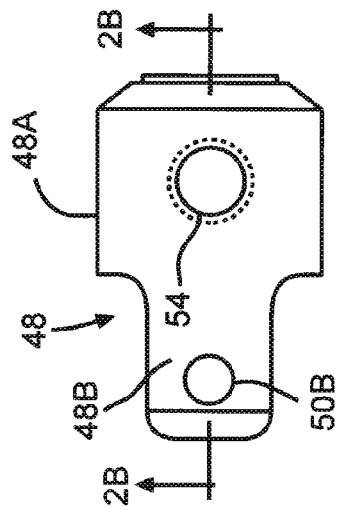
FIG. 2A is an enlarged view of a proximal U-joint 48 for the drive train 14.
Figure 2B:
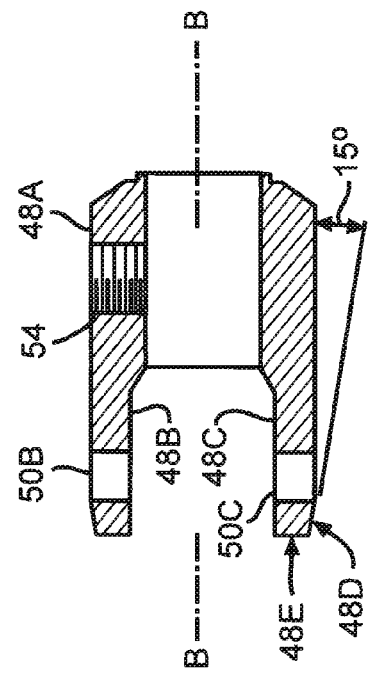
FIG. 2B is a cross-sectional view taken along line 2A-2A of FIG. 2A.

As particularly shown in FIGS. 2A and 2B, a first or proximal U-joint 48 is supported at the distal end 38A of the shaft 38. The proximal U-joint 48 is comprised of a proximal cylindrical side wall 48A supporting a pair of yoke plates 48B and 48C having respective openings 50B, 50C. Connection of the U-joint 48 to the shaft 38 is made by a screw 52, and the like. The screw is received in an opening 54 in the sidewall 48A and seats against a flat 56 at the distal shaft end 38A. In the alternative, the proximal U-joint could be welded or otherwise secured in place or, the U-joint and shaft could be machined from a single piece of material.

Figure 2C:
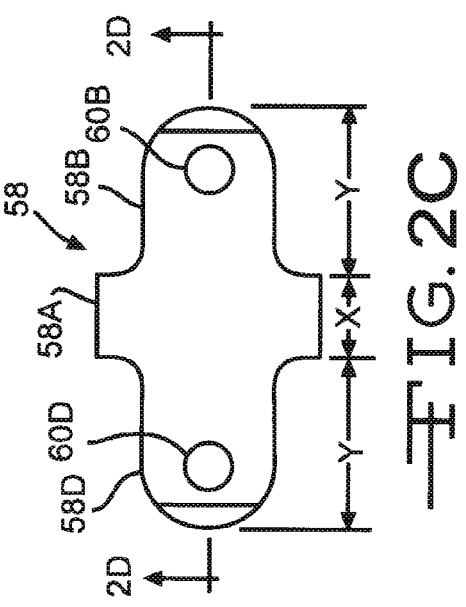
FIG. 2C is an enlarged view of an H-joint 58 for the drive train 14.
Figure 2D:
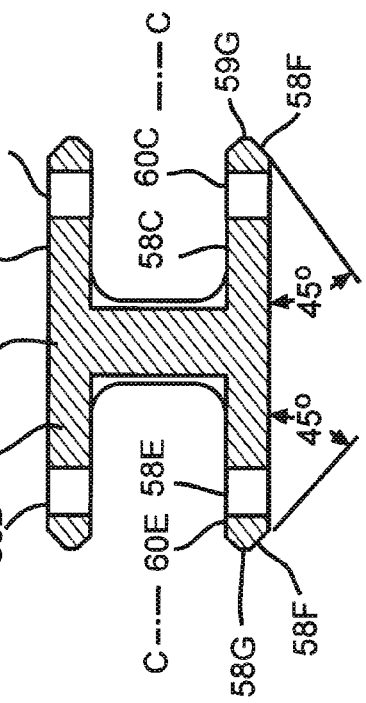
FIG. 2D is a cross-sectional view taken along line 2D-2D of FIG. 2C.

As shown in FIGS. 2C and 2D, the drive train. 14 further includes an H-shaped joint 58 comprising a cylindrical intermediate section 58A supporting opposed first and second pairs of yoke plates 58B, 58C and 58D, 58E. Respective openings 60B, 60C and 60D, 60E are provided in the yoke plates. A proximal pivot block 62 (FIG. 2) resides between the yoke plates 48B, 48C of the proximal U-joint 48 and the first pair of yoke plates 58B, 58C of the H-joint 58. The proximal pivot block 62 comprises two pairs of perpendicularly opposed openings 62A and 62B.

Pins 64A are received in the openings 50B, 50C in the yoke plates 48B and 48C of the U-joint 48 and the opening 62A in the pivot block 62, and a pin 645 is received in the opening 62B of the pivot block 62 and the openings 605, 60C of the yoke plates 58B, 58C of the H-plate 58 to thereby pivotably secure the proximal U-joint 48 to the first end of the H-joint 58. It is noted that only one of the pins 64A or 64B extends completely from one face of the pivot block 62 to the other face. As passage from one face to the other is blocked by the first pin, the other of the two pins 64A or 64B is two "half pins".

As shown in FIGS. 2E and 2F, the drive train 14 also includes a distal U-joint 66 that comprises a distal cylindrical side wall 66A supporting a pair of yoke plates 66B and 66C having respective openings 68B, 68C. Opposite the yoke plates, the cylindrical side wall 66A meets a base plate 70 having an enlarged diameter. A plurality of pins 72 extending outwardly from the base plate 70 have their respective axes aligned parallel to each other and co-axial with, but spaced from, a longitudinal axis D-D of the distal U-joint 66.

A distal pivot block 74, similar in structure to the proximal pivot block 62, comprises two pairs of perpendicularly opposed openings 74A and 74B. Pins 76A are received in the openings 68B, 68C in the respective yoke plates 66B, 66C of the distal U-joint 66 and the opening 74A in the pivot block 74, and a pin 76B is received in the openings 60D, 60E of the respective yoke plates 58D, 58E of the H-joint and opening 74B of the pivot block 74 to thereby pivotably secure the distal U-joint 66 to the second or distal end of the H-joint 58. As with the pivotable connection between the H-joint. 58 and the proximal U-joint 48, only one of the pins 76A, 76B extends the full width of the pivot block 74 from one face to an opposite face thereof. The other pin is provided as two partial length pins.

In this manner, the drive train 14 comprising the drive shaft 38, the proximal U-joint 48, the first pivot block 62, the H-joint 58, the second pivot block 74 and the distal U-joint 66 provides for transmission of rotational motion imparted to the proximal end of the shaft 38 to the base plate 70 and its supported pins 72 through a wide range of angles. The extent of this angular motion will be discussed in further detail hereinafter.

As particularly shown in FIG. 3, the base plate 70 of the distal U-joint 66 includes a central opening 78 completely through the thickness of the plate. A reamer connection crown 80 comprises a base plate 80A supporting a plurality of angled fingers 80B. Preferably, there are four angled fingers 80B. The plate 80A is provided with openings 82 that receive the pins 72 extending from the base plate 70 of the distal U-joint 66.

An abutment pin 84 is a cylindrically shaped member having a first section 84A of a lesser diameter, an intermediate section 84B of an intermediate diameter and a larger diameter third section 84C. A coil spring 86 is received on the abutment pin 84 surrounding the intermediate section 84B. The spring 86 abuts against the third section 84C. The first section 84A of the pin 84 is received in a central opening 88 in the base 80A of the reamer connection crown 80 in a fixed manner.

One end of the coil spring 86 biases against the base plate 70 of distal U-joint 66. That is on the side of the plate 70 opposite the pins 72. The other end of spring 86 biases against the larger diameter section 84C of pin 84. However, since the first section 84A of the pin 84 is fixed to the base 80A of the crown 80, the crown is thereby tensioned into a secured relationship with the distal U-joint 66. The bias of spring 86 enables the distance between the connection crown 80 against the distal U-joint 66 to be manipulated between a closely-spaced relationship and a spaced apart position.

In that manner, the reamer 12 is removably fixed to the drive train 14 by manipulating the reamer connection crown 80 in an axial direction away from the distal U-joint 66 and against the biasing force of the spring 86. This creates separation between the crown 80 and the U-joint 66, which prior to manipulation are in the closely-spaced relationship, and removes the pins 72 from blocking access to the spaces 90 provided between the fingers BOB and the crown plate 80A. The connection structure, such as the cross-bars 92 (FIG. 7) of the reamer 12, is then capable of being received in these spaces 90. When the surgeon releases his grip on the crown 80, the spring 86 returns the connection crown to its original closely-spaced relationship against the plate 70 of the distal U-joint 66. The pins 72 are once again partially residing in the spaces 90 between the fingers 80B and the base plate 80A to thereby prevent unintended release of the reamer 12 from the drive train 14 of the reamer spindle 10. This connection structure is commonly referred to as a "bayonet-type" connection.

In an assembled condition, the base plate 70 of the distal U-joint 66 seats against the forward opening 36 provided at the distal neck section 22. That is with the remaining parts of the drive train housed within the proximal and intermediate sections 20 and 24 of the housing 20. Preferably, a shaped polymeric bushing 92 is disposed between the base plate 70 and side walls 22A, 22B, 22C and 22D of the distal neck section 22 to provide a low-friction bearing surface as the drive train 14 is rotated with respect to the stationary housing 16.

Referring back to FIG. 1, the housing 16 supports a metal ring 94 on its proximal section 20. The ring 94 abuts up against a step forming a transition to the intermediate housing section 24. A plurality of proximally-facing notches 96 is spaced at regular intervals about the annular extent of the ring 94.

Figure 8:
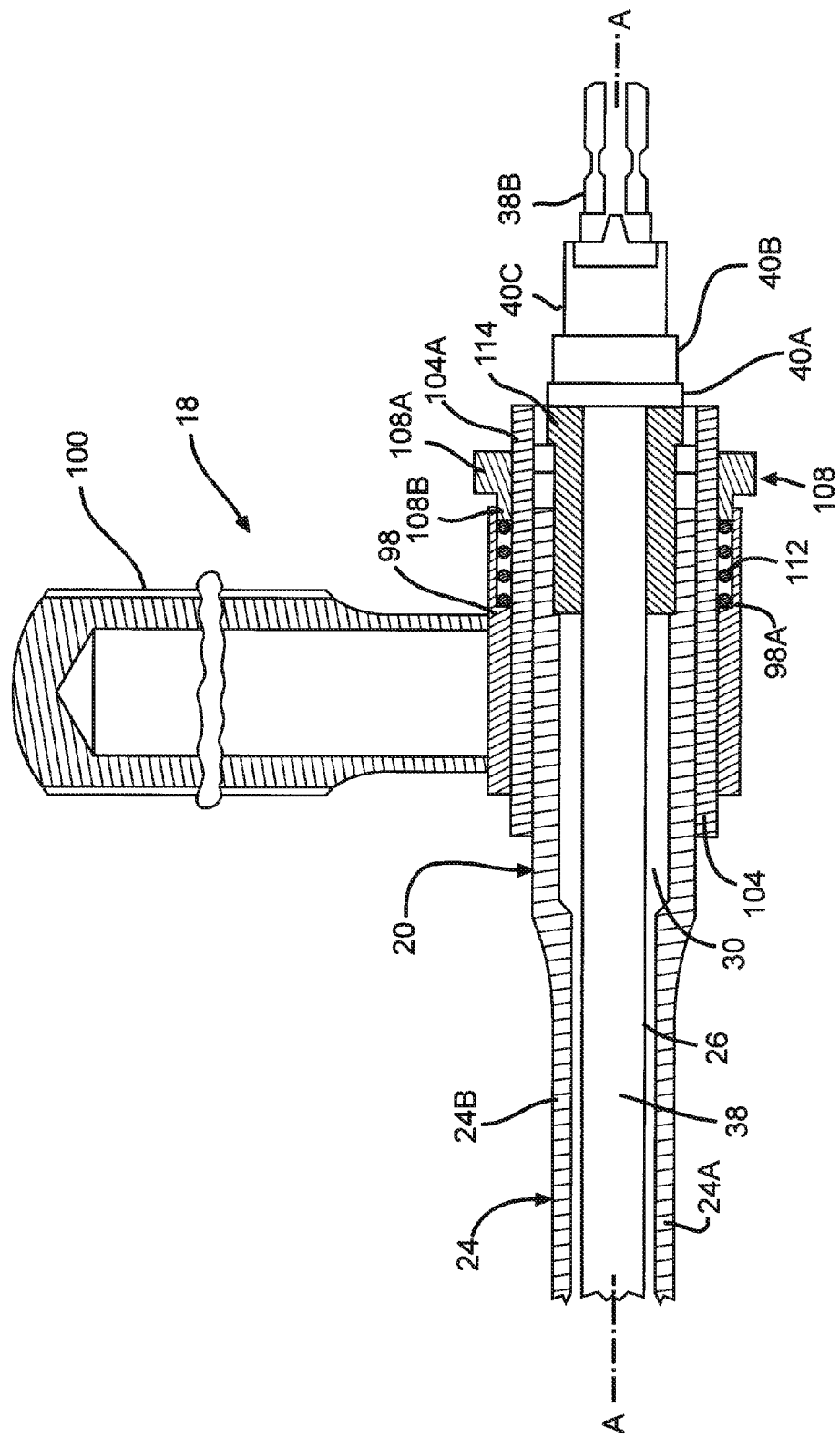
FIG. 8 is a cross-sectional view showing the handle assembly 18 connected to the proximal section 20 of the housing 16 with the drive shaft 38 of the drive train 14 contained therein.
Figure 9:
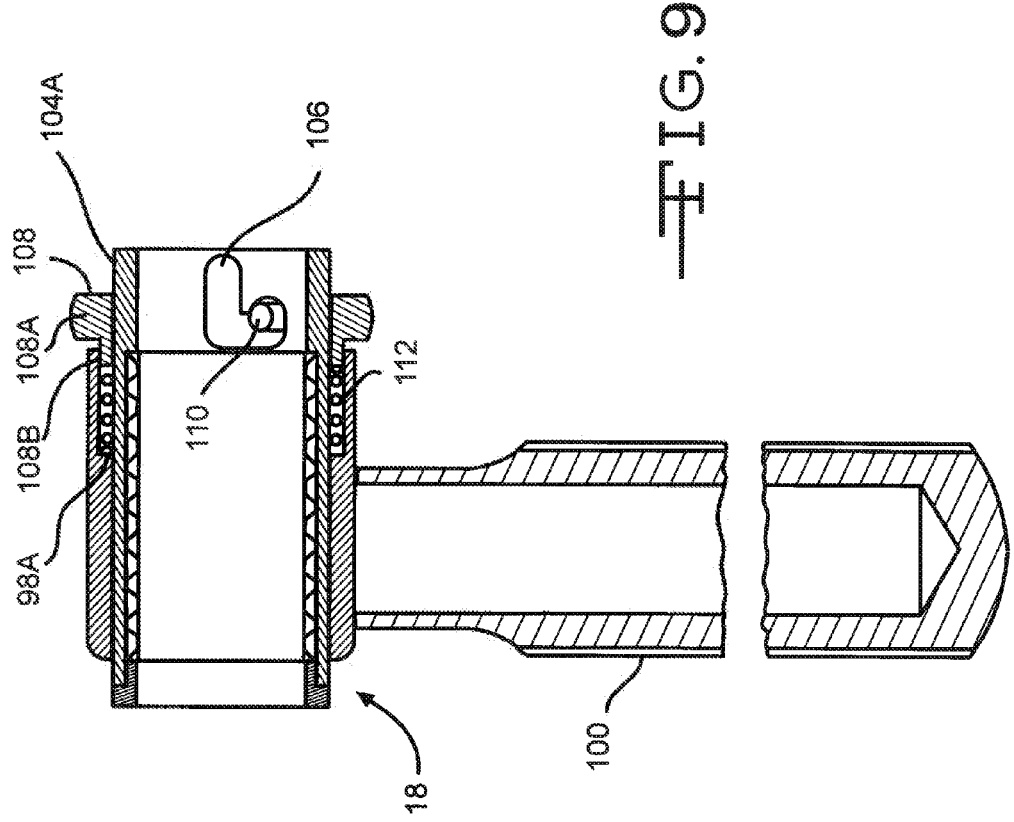
FIG. 9 is an enlarged cross-sectional view of the handle assembly 18 for the reamer spindle 10.

As shown in FIGS. 8 and 9, the handle assembly 18 comprises an outer sleeve 98 having a handle 100 fixedly secured thereto and extending in a radial or perpendicular orientation from the longitudinal axis A-A extending through the sleeve 98. At least one, and preferably two, protrusions 102 (FIG. 1) oriented diametrically opposite each other extend axially outwardly from a distal edge of the outer sleeve 98. The protrusions 102 are received in the notches 96 of the housing ring 94 to thereby connect the handle assembly 18 to the housing. However, it is desirable to be able to change the extending position of the handle assembly 18 with respect to the housing 16. That is so a surgeon can adjust the reamer assembly to a handle position that is ergonomically comfortable to him. For that purpose, any one of the protrusions 102 can fit into any one of the notches 96.

As particularly shown in FIGS. 8 and 9, an inner sleeve 104 is received inside the bore provided by the outer sleeve 98 of the handle assembly 18. The inner sleeve 104 is somewhat longer than the outer sleeve 98 to thereby provide a distally extending portion 104A. A pair of diametrically opposed J-shaped channels 106 is provided through the sidewall thickness of the extending sleeve portion 104A. A movable sleeve 108 comprises a knurled, large diameter portion 108A and a lesser diameter portion 108B. A pair of bore openings (not shown) extends from the knurled surface to the inner surface of the movable sleeve 108. The openings received pins 110 that extend inwardly past the inner sleeve surface 104. A coil spring 112 is received in an inner step 98A of the outer sleeve 98. This spring 112 biases between the step 98A and the movable sleeve 108. The pins 110 thereby confine movement of the sleeve along the J-shaped channels 106. This structure secures the movable sleeve 108 to the handle assembly 18.

Referring back to FIG. 3, a polymeric bushing 114 is provided on the drive shaft 38 between the proximal shaft portion 40 and the sleeve 42. This bushing 114 has a proximal section 114A shaped to fit between the side walls 24A, 24B of the intermediate handle section 24, and an enlarged distal section 114B. The larger diameter section 114B has a number of axial grooves 116 positioned at 90° intervals about its periphery. The proximal bushing section has an annular groove 118 that communicates with the upper one of the axial grooves 116.

To connect the handle assembly 18 to the proximal section 20 of the housing 16, the extending ends of pins 110 are moved along two of the axial channels 116 in the polymeric bushing 114 until the protrusions 102 fit into the notches 96. This puts the handle 100 in a desired orientation. Then, the knurled portion 108A of the movable sleeve 108 is rotated in a counterclockwise direction against the bias of spring 112 to move the pins 110 along the J-shaped channels 106 until the pins reside in a blind terminus end of the J-channels. In that manner, the handle assembly 18 is locked to the housing 16 with the handle 100 extending outwardly in a desired orientation and the drive train 14 secured in position inside the housing 16. To remove the handle assembly 18 from the housing 16, the movable sleeve 108 is manipulated in a reverse manner.

One unique aspect of the present reamer spindle 10 is the structure of the yoke plates comprising the proximal U-joint 48, the H-joint 58 and the distal. U-joint. As particularly shown in FIGS. 2A and 2B, the beveled surfaces 48D of the yoke plates 48B, 48C comprising the proximal U-joint 48 are at an angle of about 15° extending from at or adjacent to the respective openings 50B, 50C until the plates meet an end surface 48E that is substantially perpendicular to a longitudinal axis B-B of the U-joint 48. Axis B-B is aligned coaxially with the longitudinal axis A-A when the reamer spindle 10 is assembled having the drive train 14 housed inside the housing 16 is a functional manner.

However, the yoke plates 58B, 58C, 58D and 58E of the H-joint 58 and the yoke plates 66B and 66C comprising the distal U-joint 66 have much steeper angular shapes. As shown in FIGS. 2C and 2D for the H-joint and FIGS. 2E and 2F for the distal U-joint, the beveled surfaces 58F of the respective yoke plates 58B, 58C, 58D and 58E and the beveled surfaces 66D of the yoke plates 66B and 66C are at angles of about 45° extending from at or adjacent to the respective openings 60B, 60C, 60D, 60E and 68B, 68C until the plates meet respective end surfaces 58G and 66E.

Figure 4:
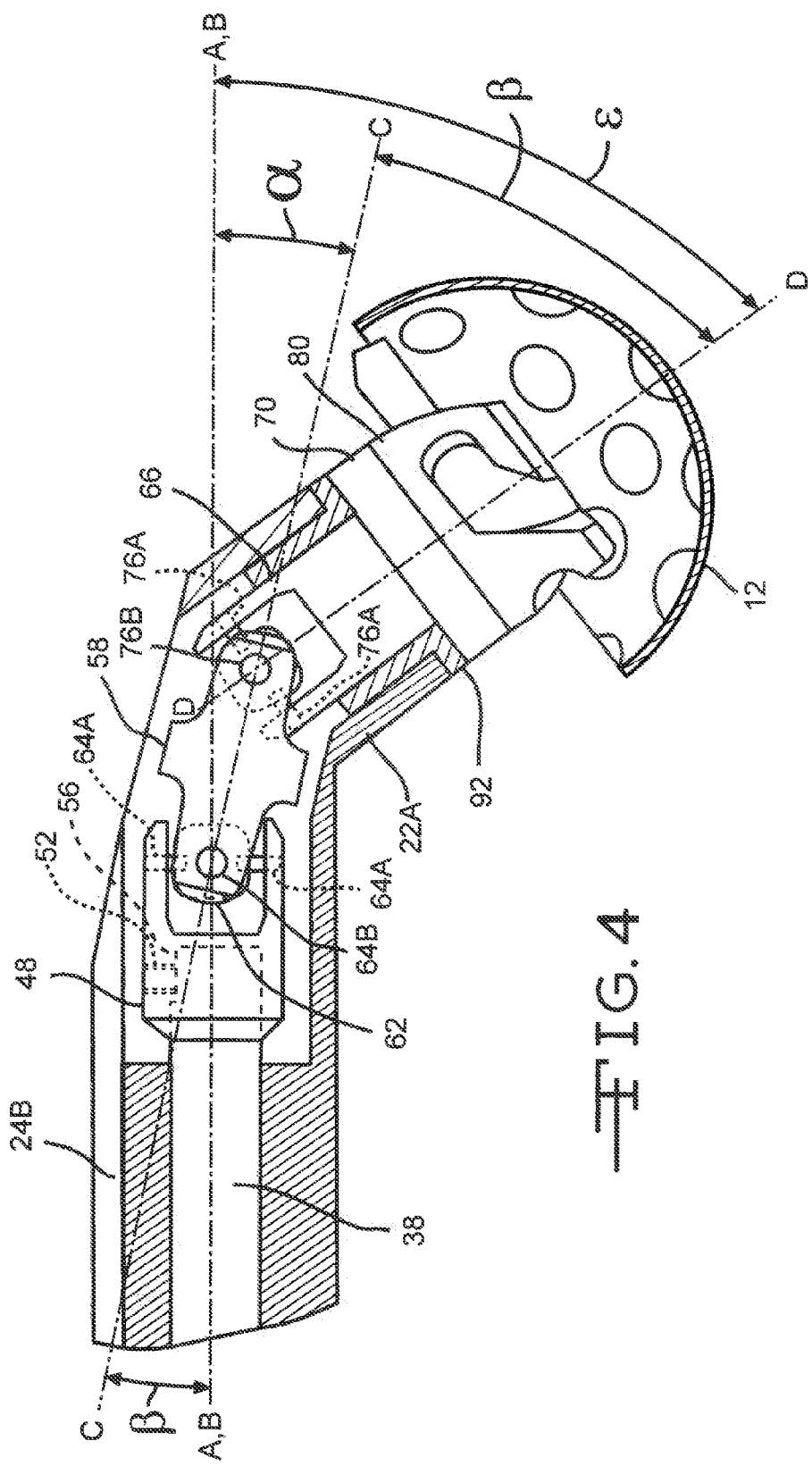
FIG. 4 is a cross-sectional view of the angular articulations of the proximal U-joint 48, H-joint 58 and distal U-joint 66 of the drive train 14 connected to a reamer 12.
Figure 5:
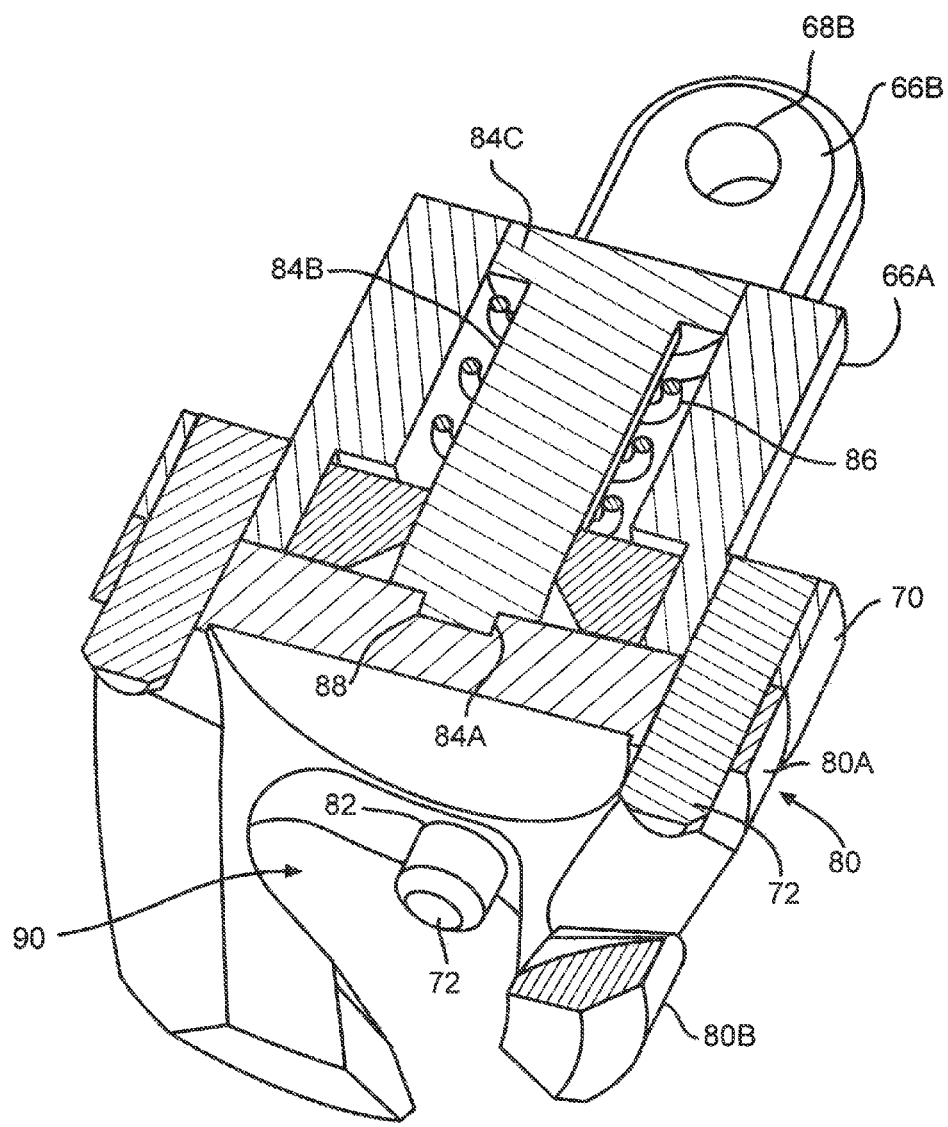
FIG. 5 is an enlarged, cross-sectional view showing the distal U-joint 66 connected to the connection crown 80.
Figure 6:
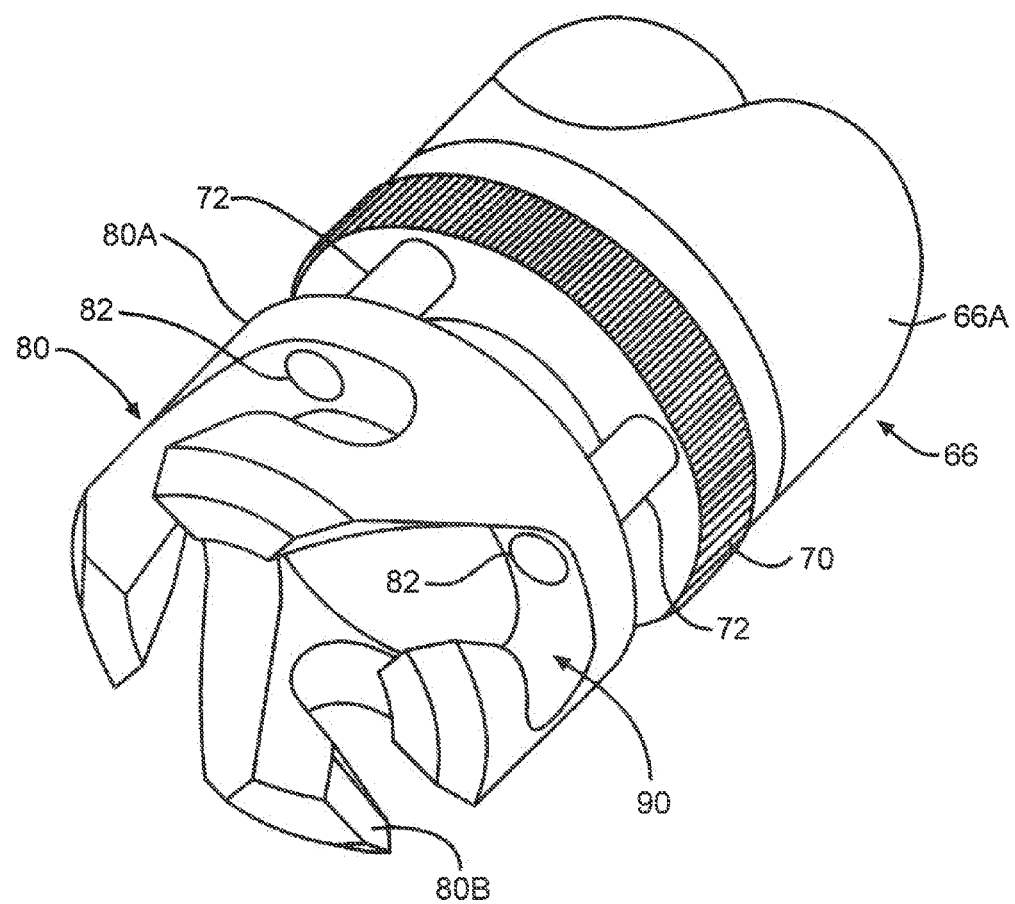
FIG. 6 is an enlarged perspective view of the reamer connection crown 80 after having been manipulated into a spaced apart relationship with the distal U-joint 66.

As shown in FIGS. 2D and 4, the beveled relationship between the proximal U-joint 48 and the H-joint 58 enables them to articulate through a range of angles α of from about 10° to about 15°, preferably about 12.5°, measured from axis C-C to the longitudinal axis A-A when the reamer spindle 10 is assembled.

Further, as shown in FIGS. 2F and 4, the beveled relationship between the H-joint 58 and the distal U-joint 66 enables the distal U-joint and, consequently, the reamer 12 to articulate through a range of angles β of from about 35° to about 45°, preferably about 42.5° measured from axis D-D to the axis C-C. The combined angular range provided by this U-joint/H-joint structure means that the distal U-joint 66 and reamer 12 are articulatable at an angle ε of from about 45° to about 60°, preferably about 55', measured from the axis D-D to the longitudinal axis A-A when the reamer spindle 10 is assembled.

Another unique aspect of the present reamer spindle 10 is the length of the intermediate section 58A of the H-joint 58 with respect to the lengths of the yoke plates 58B, 58C, 58D and 58E. The length of the intermediate section 58A is designated "x" in FIG. 2C while that of the yoke plates 58B, 58C, 58D and 58E is designated as "y". Preferably, the lengths y range from about 9 mm to about 12 mm, preferably about 10.5 mm while the length x of the intermediate section 58A is from about 3 mm to about 5 mm, preferably about 4 mm. This structure for the H-joint 58 in conjunction with the beveled surfaces of the yoke plates comprising the various U-joints 48, 66 and the H-joint 58 enables the housing 16 comprising the proximal and intermediate sections 20, 24 to be relatively long and aligned along the longitudinal axis A-A in comparison the length of the distal neck section 22. An important aspect of the distal neck section 22 is that it has a length of from about 25 mm to about 35 mm. That is without a reamer 12 secured to the drive train 14 at the end of the distal section 22 being at an angle of about 55°.

With reference to FIG. 4, what is meant by the term "distal neck section 22" is defined by an imaginary plane perpendicular to the axis D-D at the point where that axis intersects axis C-C. In other words, this imaginary plane is perpendicular to the axis of pin 76B and aligned along pins 76A.

In that manner, the present reamer spindle 10 is useful for performing MIS procedures with the drive train 14 rotating at relatively high revolutions per minute without unacceptable wobble or vibration. Having the bevel angles of the yoke plates of the proximal U-joint 48 being less than those of the H-joint 58 and the distal U-joint 66 means that the lesser a articulation angle provides a gradual transition to the greater β articulation angle. It is believed that having the lesser articulation angle α leading into the greater β angle provides greater rotational stability for that portion of the drive train 14 housed in the distal neck section 22 than if the combined articulation angle ε were the sum of two angles α and β being one-half of ε. That is especially the case with the neck section 22 being of relatively short length in comparison to the proximal and intermediate housing sections 20, 24.

Figure 10:
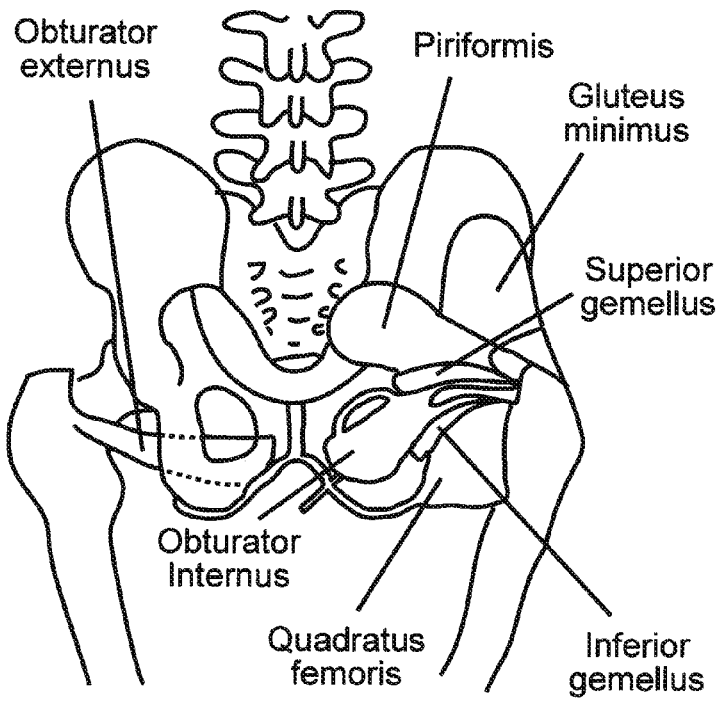
FIGS. 10 to 12 are schematic views of the anatomy of a human hip joint.
Figure 11:
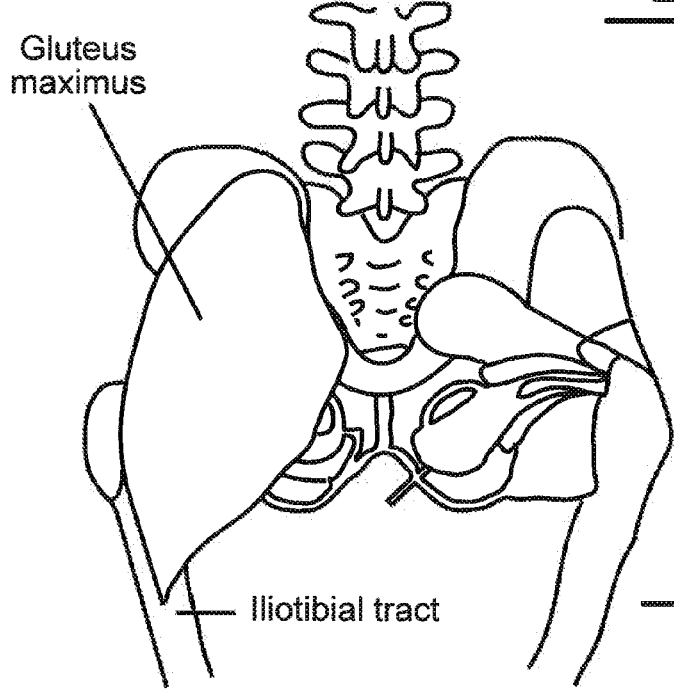
Figure 12:
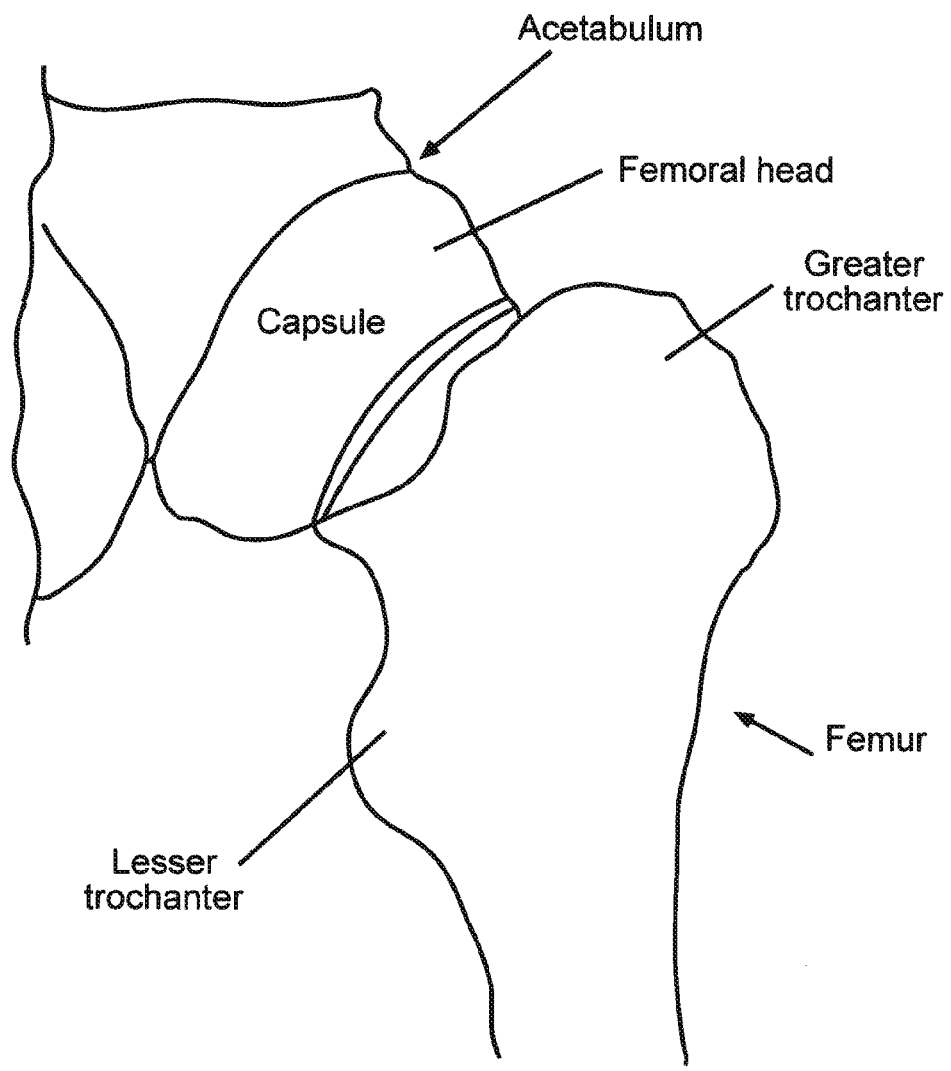

FIGS. 10 to 12 depict some features of the musculoskeletal anatomy of a human hip region. As shown in FIG. 10, there are several muscles that act to stabilize the femoral head of a femur bone in the acetabulum. Those include the short external rotator muscles (i.e., the piriformis, the superior gemellus, the obturator internus, the inferior gemellus obturator externus and the quadratus femoris). The gluteus maximus (see FIG. 11) extends over the short external rotator muscles. The femoral head is enclosed in a fibrous capsule (see FIG. 12), which attaches to the bone outside the acetabular lip and to the base of the neck of the femoral head.

The MIS posterior hip replacement approach has traditionally involved first a skin incision, followed by an incision in the fascia lata, and then detachment of the short external rotator muscles of the hip (see FIG. 10). However, in a modified MIS posterior hip replacement approach, described further below, only the piriformis muscle or conjoined tendon needs to be detached.

Figure 13:
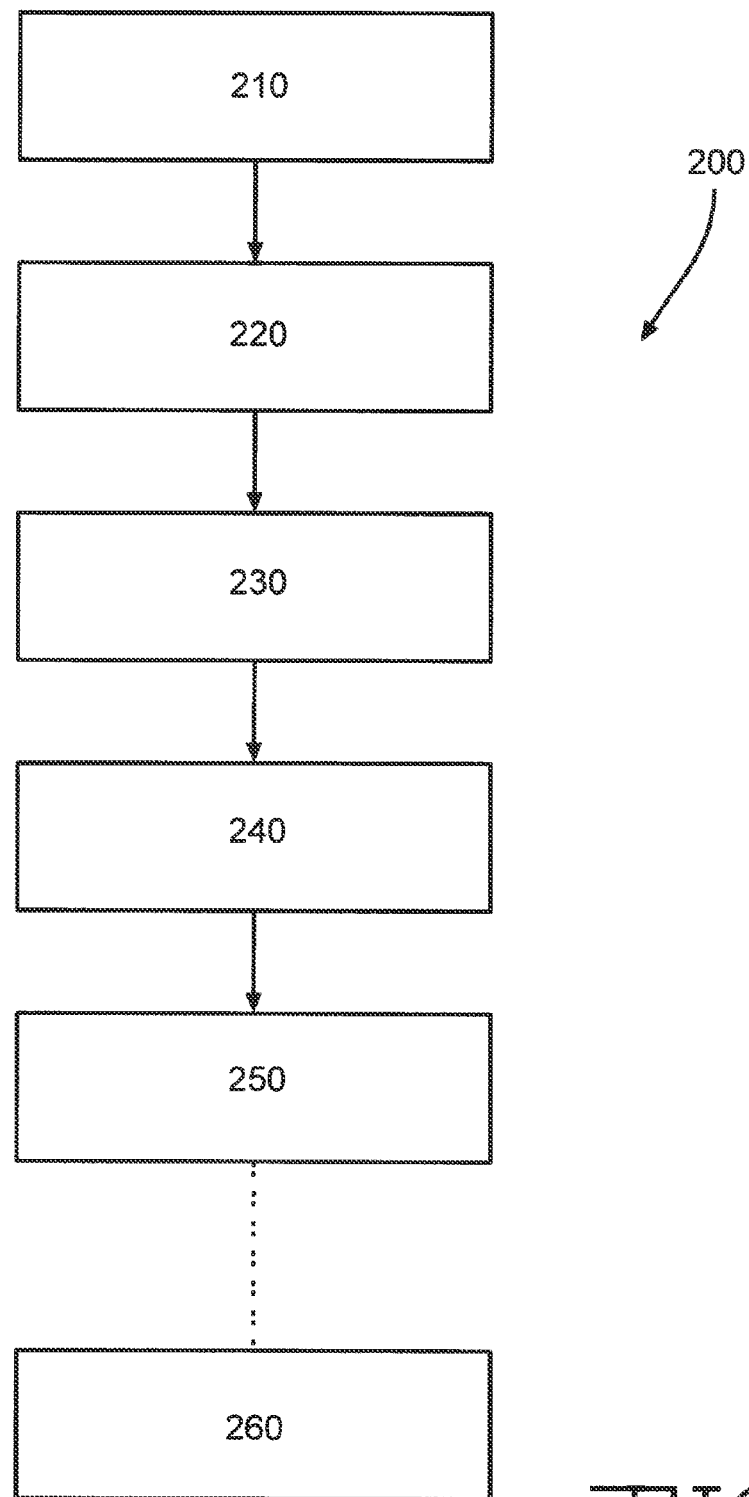
FIG. 13 is a block diagram illustrating steps in a minimally invasive hip replacement surgery using a posterior approach.
Figure 14:
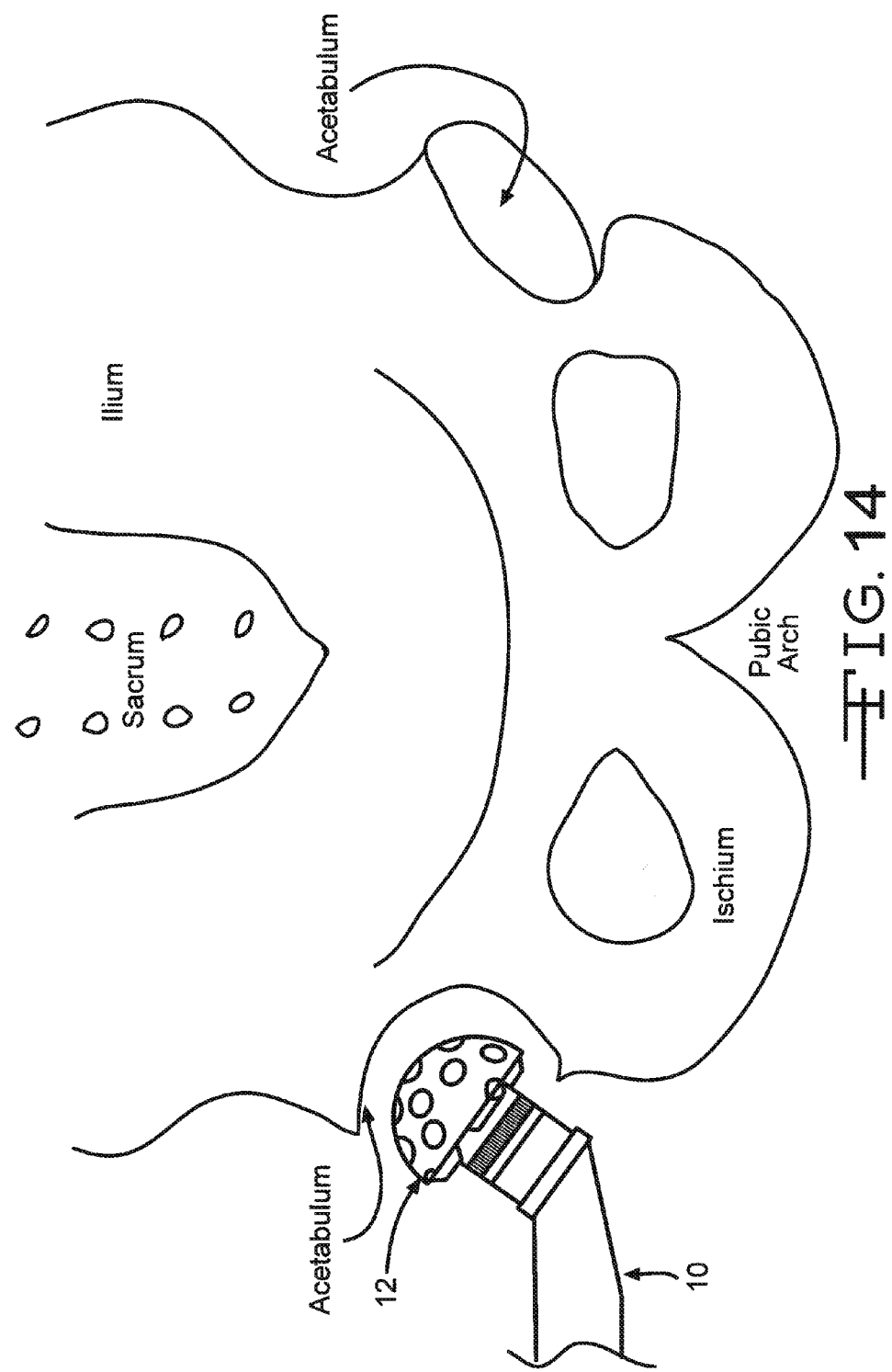
FIG. 14 is schematic view of the orientation of the reamer spindle 10 during use in a minimally invasive hip replacement surgery.

FIG. 13 is a schematic block diagram illustrating steps in a method 200 for using the reamer spindle 10 in a MIS hip replacement surgery. The surgeon begins by making an incision 210 in a posterior side of a patient's hip (e.g., on the buttocks) on a side proximate the hip joint to be treated. The surgeon then separates 220 fibers in the gluteus maximus longitudinally (i.e., not cut transversely) using a trans maximus approach to access the capsule. The present approach does not involve an incision in the fascia lata, which is required in other posterior surgical approaches. The surgeon then detaches 230 the piriformis or conjoined tendon, which is the only short external rotator muscle that is detached. This approach preserves the superior gemellus if it is not conjoined to the pirif tendon, obturator internus, inferior gemellus obturator externus and quadratus femoris, which provide significant additional stability to the hip. It is believed that such preservation also facilitates significantly faster post operative recovery. The surgeon then performs capsulotomy 240 (e.g., L-shape or J-shape) to access the acetabulum. Once access to the acetabulum is achieved, the surgeon advances 250 the distal section 22 of the reamer spindle 10 supporting the reamer 12 through the incision to the surgical site proximate the acetabulum (see FIG. 14). The reamer spindle 10 is now operated to cut bone from the acetabulum (e.g. diseased bone) and prepare the acetabulum for implantation of a prosthetic acetabular cup. The femoral head is also removed and a prosthetic hip stem implanted into the femur, the prosthetic hip stem having a femoral ball head configured to articulatingly couple to the acetabular cup prosthesis. Once the prosthesis is in place, the capsule can be closed 260, followed by closure in the incisions to the gluteus maximus and skin.

The reamer spindle 10 is preferably configured for reuse, and can be disassembled for sterilization between uses. Disassembly is done by first manipulating the movable sleeve 108 in a clockwise direction against the bias of spring 112 to move the pins 110 along the J-channels 106 and the axial channels 116 in the polymeric bushing 114 until the pins are free of the J-channels and the bushing. The handle assembly 18 is then movable in a proximal direction to remove the protrusions 102 from the notches 96 of the housing ring 94 to thereby separate the handle assembly 18 from the housing 16. The proximal portion 40 of the drive train 14 is then lifted in a lateral direction with respect to the proximal housing section 20. This separates the drive train 14 from the housing 16 with the pins 46A, 46B of sleeve 42 freeing from the vertically aligned slots 28A, 28B in the side walls 24A, 24B of the intermediate housing section 24. A further pushing force imparted to the drive train 14 causes the distal U-joint 66 to move out through the forward opening 36 provided at the distal neck section 22. The drive shaft 38 is now capable of relative movement with the housing 16 along the lower intermediate slot 32 of the intermediate housing section 24 and the open slot 34 of the distal neck section 22. However, the size of the sleeve 42 prevents the drive train 14 from being completely movable through the upper openings 26 and 30 of the respective intermediate and distal neck sections 24 and 22. Thus, the drive train 14 is separable from the housing 16 in a manner that is sufficient to clean and sterilize all of their parts without the possibility of there being total separation of one for the other. Total separation could easily lead to lost and misplaced parts.

Additionally, the housing 16 is preferably made of a durable material that can be washed and sterilized (e.g., with high heat) to comply with sterilization standards known in the art. In one embodiment, the housing 16 is made of metal, such as stainless or a super alloy material. In another embodiment, the housing 10 is made of a composite material. Though the illustrated embodiment shows the housing 16 as being one piece, in other embodiments it can be modular to facilitate disassembly of the reamer spindle 10.

Preferably, the reaming angle should correlate as closely as possible to the intended angle of acetabular cup implantation.

Additionally, as discussed above, the length of the distal neck section 22 is preferably between about 25 mm and about 35 mm. This range is particularly advantageous in MIS hip replacement surgical procedures (e.g., the method illustrated in FIG. 13) in that during the surgical procedure the distal neck section 22 is in direct contact with the short external rotator muscles, which must be preserved to optimize the clinical outcome. The length of approximately 25-35 mm advantageously allows the reamer 12 to be positioned within the acetabulum while minimizing contact between the reamer spindle 10 (e.g., the distal neck section 22) and the short external rotator muscles of the hip, which are in the inferior aspect of the wound. Additionally, the thickness (e.g., outer diameter) of the housing 16, which is preferably between about 9 mm and about 16 mm also advantageously minimizes soft tissue trauma during advancement of the reamer spindle 10 through the incision to position the reamer 12 within the acetabulum.

Through the reamer spindle 10 is discussed above in connection with an MIS hip replacement posterior approach, one of the ordinary skill in the art will recognize that the reamer spindle 10 can be used in other MIS hip replacement surgical approaches, such as the anterior, antero-lateral, and postero-lateral approaches. Additionally, the reamer spindle 10 may also be usable in applications other than posterior MIS hip replacement procedures such as interior, interior-lateral and postero-lateral approaches, as well as shoulder replacement procedures. Though use of the reamer spindle 10 is described herein with respect to human hip replacement surgery, one of ordinary skill in the art will recognize that it may also be useful in animal hip replacement surgeries.

Of course, the foregoing description is that of certain features, aspects and advantages of the present invention, to which various changes and modifications can be made without departing from the spirit and scope of the present invention. Moreover, the reamer need not feature all of the objects, advantages, features and aspects discussed above. For example, in some embodiments, the casing of the reamer in the neck portion can be removed and/or replaced with a shield member to inhibit trauma to muscle tissue during operation of the reamer. Thus, for example, those of skill in the art will recognize that the invention can be embodied or carried out in a manner that achieves or optimizes one advantage or a group of advantages taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention.

What is claimed is:

1. A surgical reamer spindle, which comprises:
   a) a housing comprising a housing length extending along a first longitudinal axis from a proximal housing portion to a distal housing neck portion that is disposed at an acute angle with respect to the first longitudinal axis;
   b) a drive train at least partially housed within the housing, the drive train comprising;
      i) a drive shaft extending along the first longitudinal axis and comprising a proximal drive shaft end adapted for releasable connection to a rotary motion source and a distal drive shaft end;
      ii) a proximal U-joint connected to the distal drive shaft end, the proximal U-joint extending along the first longitudinal axis and comprising a pair of forwardly-extending first yoke plates, each first yoke plate having a first opening and a first beveled exterior surface, wherein each of the first beveled exterior surfaces extends inwardly and downwardly toward the first longitudinal axis from, at, or adjacent to the respective first opening to a distal end of the respective first yoke plate;
      iii) an H-joint extending along a second longitudinal axis at a first acute angle with respect to the first longitudinal axis, the H-joint comprises an intermediate section connected to second and third pairs of yoke plates which oppose one another, each yoke plate of the second pair has a respective second opening and second beveled exterior surface, and each yoke plate of the third pair has a respective third opening and third beveled exterior surface, wherein each of the second and third beveled exterior surfaces extends inwardly and downwardly toward the second longitudinal axis from, at, or adjacent to the respective second and third openings to: (a) a proximal end of the respective second yoke plate, and (b) a distal end of the respective third yoke plate, respectively, and wherein each yoke plate of the second and third pairs has a yoke plate length y that is greater than an intermediate length x of the intermediate section of the H-joint;
      iv) a distal U-joint extending along a third longitudinal axis at a second acute angle with respect to the first longitudinal axis, the distal U-joint comprising a pair of rearwardly-extending fourth yoke plates, each fourth yoke plate having a fourth opening and a fourth beveled exterior surface, wherein each of the fourth beveled exterior surfaces extends inwardly and downwardly toward the third longitudinal axis from, at, or adjacent to the respective fourth opening to a proximal end of the respective fourth yoke plate, and wherein the distal U-joint comprises a distal portion of the drive train residing in the distal housing neck portion; and v) wherein the second pair of yoke plates of the H-joint are pivotably connected to respective ones of the forwardly-extending first yoke plates of the proximal U-joint and the third pair of yoke plates of the H-joint are pivotably connected to respective ones of the rearwardly-extending fourth yoke plates of the distal U-joint; and c) wherein rotational movement imparted to the proximal drive shaft end causes rotation of the proximal U-joint connected to the H-joint connected to the distal U-joint and a reamer releasably connected thereto.

2. The reamer spindle of claim 1 wherein the forwardly-extending first yoke plates of the proximal U-joint extend to respective terminal ends that are substantially perpendicular to the first longitudinal axis.

3. The reamer spindle of claim 1 wherein the fourth beveled exterior surfaces of the respective rearwardly-extending fourth yoke plates of the distal U-joint extend to respective terminal ends that are substantially perpendicular to the third longitudinal axis.

4. The reamer spindle of claim 1 wherein the distal housing neck portion is offset from 45° to 60° with respect to the first longitudinal axis.

5. The reamer spindle of claim 1 further including:
i) a housing ring supported on the proximal housing portion, the housing ring comprising a proximal face having a notch provided therein;
ii) an inner handle sleeve disposed inside a co-axial outer handle sleeve, wherein the inner handle sleeve has an axial length that is longer than that of the outer handle sleeve to thereby provide an inner handle sleeve extension portion;
iii) a handle supported on the outer handle sleeve;
iv) a locking ring supported on the inner handle sleeve, the locking ring having a locking ring pin aligned perpendicular to a co-axis of the inner and outer handle sleeves, the locking ring pin being received in a J-shaped channel provided in the inner handle sleeve extension portion to thereby capture the locking sleeve between the inner and outer handle sleeves;
v) a biasing member captured between the inner and outer handle sleeves and biasing against the locking ring,
vi) wherein a proximal portion of the drive shaft comprises an axial channel extending distally from and adjacent to the proximal drive shaft end and meeting an annular drive shaft groove, and
vii) wherein the inner and outer handle sleeves including the locking ring are adapted to slide over the proximal housing portion to seat the locking ring pin in the notch of the housing ring, and then the locking ring is manipulatable to move the locking ring pin along the J-shaped channel in the inner handle sleeve and simultaneously along an axial groove in the drive shaft and then the locking ring is manipulatable in a rotational manner to move the locking ring pin out of alignment with the axial groove and along the annular groove in the drive shaft and further along the J-shaped channel against the biasing member to thereby lock the inner and the outer handle sleeves supporting the handle in one of several adjustable locations with respect to the housing and the drive train.

6. The reamer spindle of claim 5 wherein the J-shaped channel in the inner handle sleeve is spaced distally from a proximal inner handle sleeve end.

7. The reamer spindle of claim 5 wherein there are two diametrically opposed J-shaped channels in the inner handle sleeve.

8. The reamer spindle of claim 7 wherein the locking ring has two locking ring pins oriented perpendicular to the first longitudinal axis and aligned diametrically opposite each other and wherein the diametrically opposed locking ring pins are adapted to move along the diametrically opposed J-shaped channels in the inner handle sleeve as the locking ring is manipulated.

9. The reamer spindle of claim 5 wherein a fourth longitudinal axis of the handle is perpendicular to the first longitudinal axis of the drive shaft.

10. The reamer spindle of claim 1 wherein the first beveled exterior surface is 15° relative to the first longitudinal axis.

11. The reamer spindle of claim 1 wherein the second and third beveled exterior surfaces are angled at 45° relative to the second longitudinal axis for the H-joint and the third longitudinal axis for the distal U-joint.

12. The reamer spindle of claim 1 wherein the distal end of the proximal U-joint is substantially perpendicular to the first longitudinal axis.

13. The reamer spindle of claim 1 wherein the first acute angle measures from 10° to 15°.

14. The reamer spindle of claim 1 wherein the first acute angle is 12.5°.

15. The reamer spindle of claim 1 wherein the second acute angle measures from 35° to 45°.

16. The reamer spindle of claim 1 wherein the second acute angle is 42.5°.

17. The reamer spindle of claim 1 wherein the length y ranges from 9 mm to 12 mm and the length x from 3 mm to 5 mm.

18. The reamer spindle of claim 1 wherein the housing comprises an H-joint area containing the H-joint, the H-joint area having a length ranging from 25 mm to 35 mm extending along the second longitudinal axis.

19. The reamer spindle of claim 1 wherein a bayonet fitting extends distally from the distal U-joint for releasable connection to the reamer.

20. The reamer spindle of claim 1 wherein the distal U-joint is releasably connectable to the reamer through a reamer connection crown.

21. The reamer spindle of claim 1 wherein the distal housing neck portion is disposed at an angle greater than 30° with respect to the first longitudinal axis.

22. The reamer spindle of claim 1 wherein each of the second, third and fourth beveled exterior surfaces extends inwardly and downwardly toward their respective second and third longitudinal axes at an equal angle.

23. The reamer spindle of claim 1 wherein each of the second, third and fourth beveled exterior surfaces extends inwardly and downwardly toward their respective second and third longitudinal axes at an angle that is greater than the angle which the first beveled exterior surfaces of the first yoke plates extends inwardly and downwardly toward the first longitudinal axis.

24. A reamer spindle, comprising:
a) a housing comprising a housing length extending along a first longitudinal axis from a proximal housing portion to a distal housing neck portion that is disposed at an angle greater than 30° with respect to the first longitudinal axis;
b) a drive train at least partially housed within the housing, the drive train comprising:

i) a drive shaft extending along the first longitudinal axis and comprising a proximal drive shaft end adapted for releasable connection to a rotary motion source and a distal drive shaft end;

ii) a proximal U-joint connected to the distal drive shaft end, the proximal U-joint extending along the first longitudinal axis and comprising a pair of forwardly-extending first yoke plates, each first yoke plate having a first opening and a first beveled exterior surface, wherein each of the first beveled exterior surfaces extends inwardly and downwardly toward the first longitudinal axis at an angle of 15° from, at, or adjacent to the respective first opening to a distal end of the respective first yoke plate;

iii) an H-joint extending along a second longitudinal axis at an angle of 12.5° with respect to the first longitudinal axis, the H-joint comprising an intermediate section connected to second and third pairs of yoke plates which oppose one another, each yoke plate of the second pair has a respective second opening and second beveled exterior surface, and each yoke plate of the third pair has a respective third opening and third beveled exterior surface, wherein each of the second and third beveled exterior surfaces extends inwardly and downwardly toward the second longitudinal axis at an angle of 45° from, at, or adjacent to the respective second and third openings to: (a) a proximal end of the respective second yoke plate, and (b) a distal end of the respective third yoke plate, respectively, and wherein each yoke plate of the second and third pairs has a yoke plate length ranging from 9 mm to 12 mm and the intermediate section of the H-joint has a length ranging from 3 mm to 5 mm;

iv) a distal U-joint extending along a third longitudinal axis at a second acute angle with respect to the first longitudinal axis, the distal U-joint comprising a pair of rearwardly-extending fourth yoke plates, each fourth yoke plate having a fourth opening and a fourth beveled exterior surface, wherein each of the fourth beveled exterior surfaces extends inwardly and downwardly toward the third longitudinal axis at an angle of 45° from, at, or adjacent to the respective fourth opening to a proximal end of the respective fourth yoke plate, wherein the distal U-joint comprises a distal portion of the drive train residing in the distal housing neck portion, and v) wherein the second pair of yoke plates of the H-joint are pivotably connected to respective ones of the forwardly-extending first yoke plates of the proximal U-joint through pivot pins received in the respective second and first openings and an intermediate first pivot block, and the third pair of yoke plates of the H-joint are pivotably connected to respective ones of the rearwardly-extending fourth yoke plates of the distal U-joint through pivot pins received in the respective third and fourth openings and an intermediate second pivot block; and c) wherein rotational movement imparted to the proximal drive shaft end causes rotation of the proximal U-joint connected to the H-joint connected to the distal portion of the drive train including the distal U-joint and a reamer releasably connected thereto.

\* \* \* \* \*

UNITED STATES PATENT AND TRADEMARK OFFICE
CERTIFICATE OF CORRECTION

PATENT NO.       : 8,480,674 B1
APPLICATION NO.  : 13/187924
DATED            : July 9, 2013
INVENTOR(S)      : Roger et al.

Page 1 of 1

It is certified that error appears in the above-identified patent and that said Letters Patent is hereby corrected as shown below:

In the Claims

Column 10, line 24, Claim 1, delete ";" and insert --:--

Column 12, line 33, Claim 17, insert --ranges-- between the letter "x" and the word "from"

Signed and Sealed this
Third Day of June, 2014

Michelle K. Lee
*Deputy Director of the United States Patent and Trademark Office*